United States Patent [19]
Manabe

[11] Patent Number: 5,292,482
[45] Date of Patent: Mar. 8, 1994

[54] AUTOMATIC ANALYZING APPARATUS AND AUTOMATIC ANALYZING METHOD

[75] Inventor: Sugio Manabe, Tokyo, Japan

[73] Assignee: Olympus Optical Co., Ltd., Tokyo, Japan

[21] Appl. No.: 828,348

[22] Filed: Jan. 30, 1992

[30] Foreign Application Priority Data

Feb. 7, 1991 [JP] Japan .................. 3-016631

[51] Int. Cl.⁵ .................. G01N 31/00; G01N 35/06
[52] U.S. Cl. .................. 422/64; 422/50; 422/63; 436/43; 436/47
[58] Field of Search .................. 422/62, 63, 64, 65, 422/67, 100, 104, 65, 50; 436/43, 47

[56] References Cited

U.S. PATENT DOCUMENTS

| | | | |
|---|---|---|---|
| 4,077,444 | 3/1978 | Gilson et al. | 422/65 |
| 4,168,955 | 9/1979 | Allington | 422/65 |
| 4,170,625 | 10/1979 | Welch | 422/64 |
| 4,675,162 | 6/1987 | Sakamaki et al. | 422/65 |
| 4,727,033 | 2/1988 | Hijikata et al. | 422/65 |
| 4,767,716 | 8/1988 | Sakamaki et al. | 422/65 |
| 4,785,407 | 11/1988 | Sakagami | 422/64 |
| 4,908,320 | 3/1990 | Zakowski et al. | 422/64 |
| 5,037,612 | 8/1991 | Takahasi et al. | 422/64 |

FOREIGN PATENT DOCUMENTS

| | | |
|---|---|---|
| 0100663 | 2/1984 | European Pat. Off. . |
| 0316766 | 5/1989 | European Pat. Off. . |
| 0355823 | 2/1990 | European Pat. Off. . |
| 0356569 | 3/1990 | European Pat. Off. . |
| 3016294 | 10/1981 | Fed. Rep. of Germany . |
| 3908725 | 9/1990 | Fed. Rep. of Germany . |
| 59-24380 | 6/1984 | Japan . |
| 0247971 | 10/1986 | Japan . |

Primary Examiner—James C. Housel
Assistant Examiner—Ramon Torres
Attorney, Agent, or Firm—Frishauf, Holtz, Goodman & Woodward

[57] ABSTRACT

An automatic analyzing apparatus of this invention has first and second reaction container holders, a photometric unit, and a control unit. Each of the first and second reaction container holders is movable along a reaction line and has a plurality of reaction containers to which a liquid sample such as blood or urine can be injected. The photometric unit has a function of optically analyzing a concentration of a chemical component of the liquid sample injected in the reaction containers of the first and second reaction container holders when the first and second reaction container holders pass through it. A control unit has a function of stopping only either one of the first and second reaction container holders on the reaction line and moving the other reaction container holder along the reaction line to pass through the photometric unit.

18 Claims, 7 Drawing Sheets

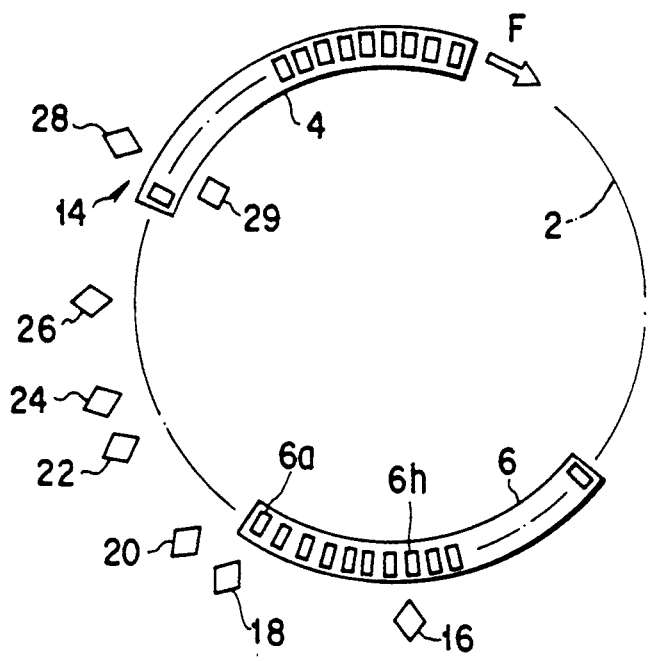
F I G. 9
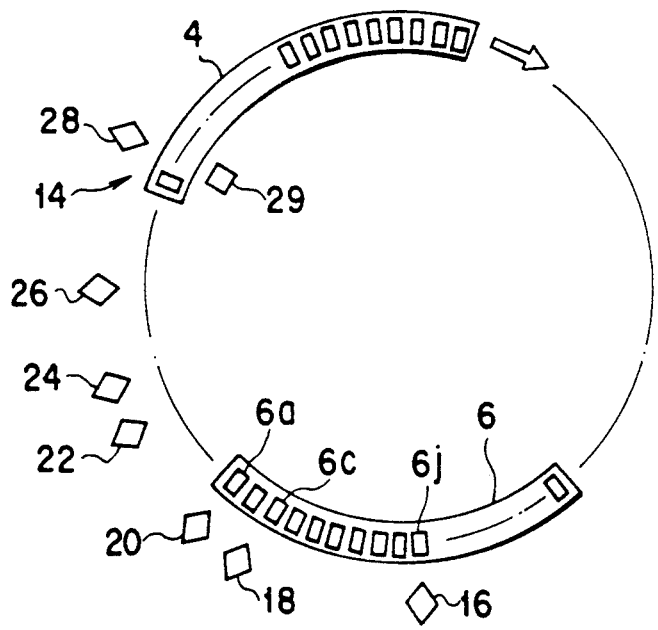
F I G. 10

AUTOMATIC ANALYZING APPARATUS AND AUTOMATIC ANALYZING METHOD

BACKGROUND OF THE INVENTION

1. Field of the Invention

The present invention relates to an automatic analyzing apparatus and an automatic analyzing method for performing quantitative measurement of the concentrations of chemical components of a liquid sample such as blood and urine.

2. Description of the Related Art

Conventionally, a biochemical automatic analyzing apparatus and an automatic analyzing method for performing quantitative measurement of the concentrations of chemical components of a liquid sample have been widely used in medical diagnosis.

Recently, as the number of cases to be processed and the number of measurement items are increased, an increase in processing capabilities of the apparatus and method is demanded.

In order to cope with this demand, Published Examined Japanese Patent Application No. 59-24380 (to be merely referred to as a cited reference hereinafter) discloses a chemical analyzing apparatus and a chemical analyzing method having characteristic features as follows.

The apparatus of this cited reference has a convey unit (control unit) for rotating or stopping rotating a plurality of reaction containers (capable of containing a liquid sample) arranged in a loop manner and a photometer for optically measuring the reaction process of the liquid sample contained in the reaction containers during rotation of the reaction containers.

More specifically, for example, a liquid sample and a reaction reagent are discharged into a first reaction container located at a discharge position, and thereafter the convey unit is driven to rotate the plurality of reaction containers counterclockwise. During this rotation, the optical characteristic value in the first reaction container which has passed across the optical path of the photometer is measured. The reaction process of the sample is detected on the basis of this optical characteristic value.

Then, when the plurality of reaction containers are stopped, a second reaction container next to the first reaction container is placed at the discharge position, and the liquid sample and the reaction reagent are discharged in the second reaction container.

Reaction containers to which injection of the liquid sample and the reagent, agitation, and measurement have been done are sequentially cleaned with cleaning water sprayed from a cleaning nozzle.

In the apparatus of the cited reference, however, when, e.g., the rotation time of the plurality of reaction containers is decreased (i.e., the rotational speed is increased) in order to improve the analyzing efficiency, the light-measuring time of a reaction containers is decreased. As a result, the light-measuring precision is considerably degraded.

When the stop time of the plurality of reaction containers is decreased in order to improve the analyzing efficiency, the cleaning precision of a reaction container after measurement is degraded. As a result, a newly discharged liquid sample is contaminated by the liquid sample attached to the previous reaction container, and the analyzing precision is considerably degraded.

In order to solve these problems, when the reaction containers are stopped, the photometer may be moved along the array of the plurality of reaction containers to detect the reaction process of the liquid sample and the reagent.

However, when a means for moving a photometric unit having a light source and a spectroscope is provided, the size of the analyzing apparatus as a whole is increased. The moving speed is limited because of the structure of the apparatus.

SUMMARY OF THE INVENTION

The present invention has been made in order to solve the problems described above, and has as its object to provide an automatic analyzing apparatus capable of improving the analysis processing capability while maintaining sufficient light-measuring time, agitating time, and cleaning time to ensure the analyzing precision.

According to the present invention, while one reaction container holder is moved, the chemical component concentrations of a liquid sample or a reagent of reaction containers of this reaction container holder are optically analyzed. During this period of time, the other reaction container holder is held at a predetermined position, and a liquid sample or a reagent is injected into the reaction containers of this holder.

That is according to the apparatus of the present invention, within the same analysis time as that of the conventional apparatus, rotation time and stop time which are sufficiently longer than those of the conventional apparatus can be obtained.

As a result, according to the apparatus of the present invention, a high light-measuring precision can be maintained, and the reaction containers can be sufficiently cleaned. Hence, a considerably high analyzing precision of the apparatus can be maintained.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 9 is a view showing a state in which only the second reaction container holder is stopped, its first reaction container is placed at a liquid sample injecting portion, and its eighth reaction container is placed at the first reagent injecting portion;

FIG. 10 is a view showing a state in which only the second reaction container holder is stopped, its first reaction container is placed at a first agitating portion, its third reaction container is placed at the liquid sample injecting portion, and its tenth reaction container is placed at the first reagent injecting portion;

DETAILED DESCRIPTION OF THE PREFERRED EMBODIMENTS

A preferred embodiment of an automatic analyzing apparatus of the present invention will be described with reference to the accompanying drawings.

Figure 1:
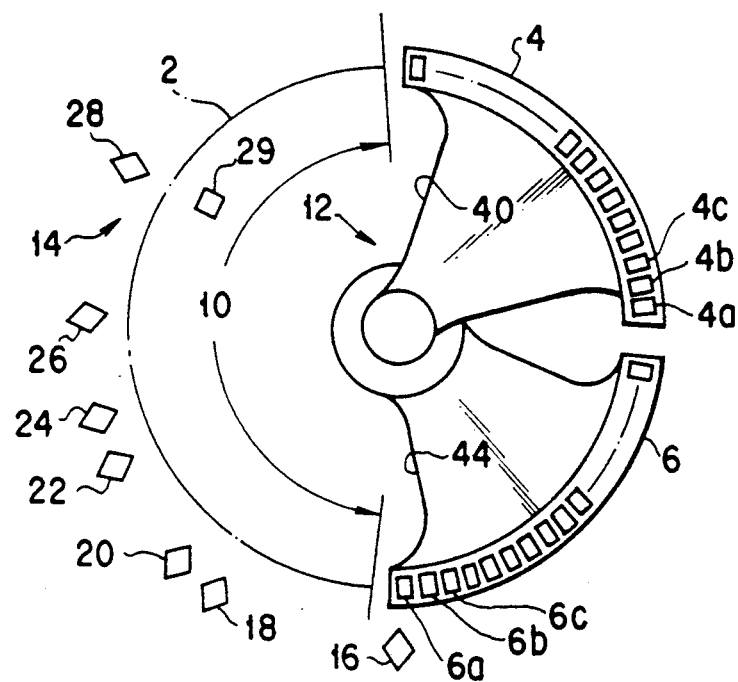
FIG. 1 is a plan view showing an arrangement of an automatic analyzing apparatus according to an embodiment of the present invention.

As shown in FIG. 1, in the automatic analyzing apparatus of this embodiment, first and second reaction container holders 4 and 6 are provided to be movable along an annular closed loop reaction line 2. The first and second reaction container holders 4 and 6 have the same radius of curvature as that of the reaction line 2, and each of them forms an arc corresponding to $\frac{1}{4}$ the circumferential length of the reaction line 2. A plurality of reaction containers $4a, 4b, 4c, \ldots$, and $6a, 6b, 6c, \ldots$ are provided in the reaction container holders 4 and 6, respectively. The reaction containers $4a, 4b, 4c \ldots$, and $6a, 6b, 6c, \ldots$ have such a form to contain a liquid sample, e.g., blood and urine, or a reagent therein and are made of a material which allows optical measurement.

Of the entire length of the reaction line 2, the length of a portion excluding a total length of the first and second reaction container holders 4 and 6 corresponds to $\frac{1}{2}$ the entire length of the reaction line 2. As a result, an empty portion 10 is formed at this remaining portion of the reaction line 2, i.e., between the first and second reaction container holders 4 and 6.

The automatic analyzing apparatus of this embodiment has a control unit 12 for controlling clockwise rotation and stop of the first and second reaction container holders 4 and 6, and a photometric unit 14 for performing optical analysis of the concentrations of the chemical components of the liquid sample injected in the plurality of reaction containers $4a, 4b, 4c, \ldots$, and $6a, 6b, 6c, \ldots$ during rotation of the first and second reaction container holders 4 and 6.

The photometric unit 14 has a light source 28 and a light-receiving section 29 for receiving light (having a predetermined optical characteristic) emitted from the light source 28.

In the automatic analyzing apparatus of this embodiment, a first reagent injecting portion 16, a liquid sample injecting portion 18, a first agitating portion 20, a second reagent injecting portion 22, a second agitating portion 24, and a cleaning portion 26 are provided along the reaction line 2. At the first reagent injecting portion 16, a first reagent is injected into the plurality of reaction containers $4a, 4b, 4c, \ldots$, and $6a, 6b, 6c, \ldots$. At the liquid sample injecting portion 18, a liquid sample such as blood and urine is injected into a reaction container in which the first reagent has been contained. At the first agitating portion 20, the first reagent and the liquid sample are agitated. At second reagent injecting portion 22, a second reagent is injected. At the second agitating portion 24, the first reagent, the liquid sample, and the second reagent are agitated. At the cleaning portion, a reaction container analysis of which is completed is cleaned.

Figure 2:
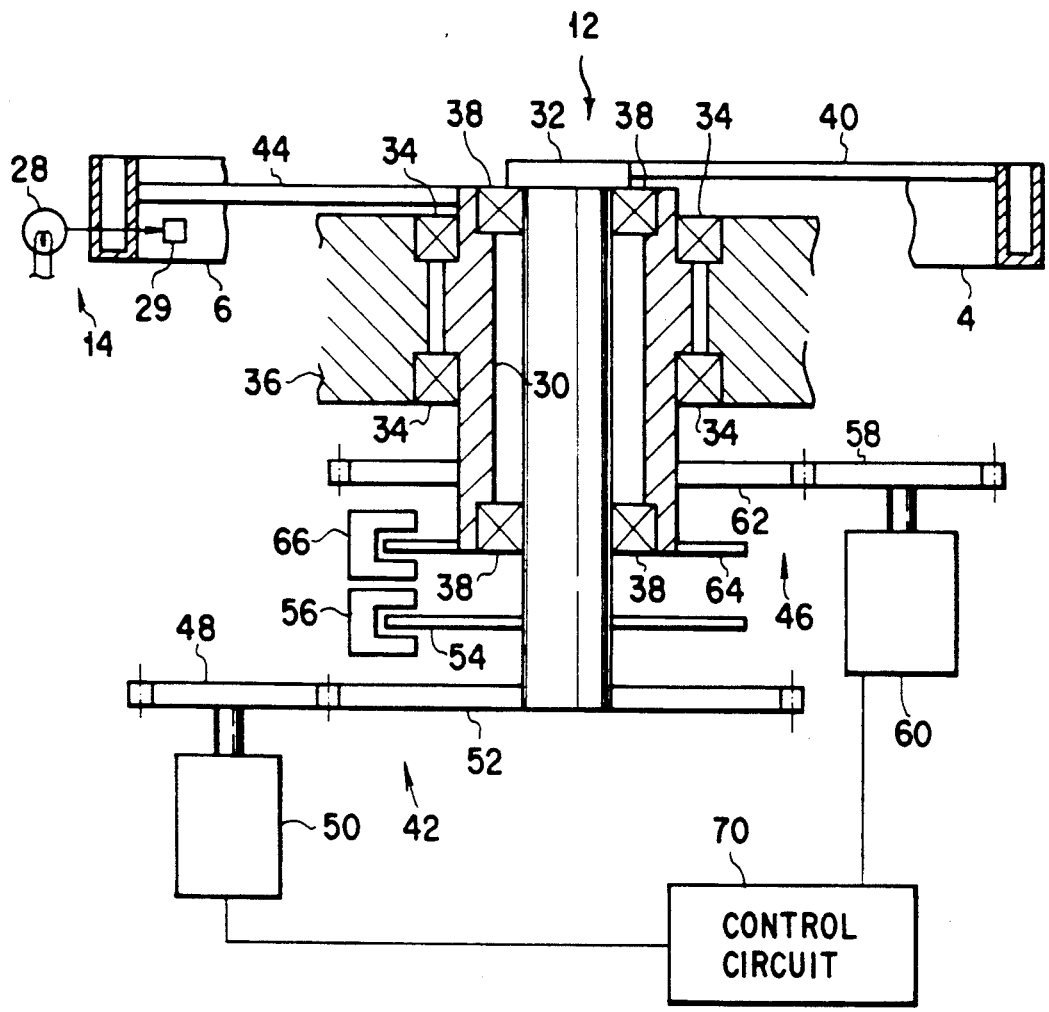
FIG. 2 is a sectional view showing an arrangement of a control unit arranged in the automatic analyzing apparatus.

FIG. 2 schematically shows the entire arrangement of the control unit 12 described above.

As shown in FIG. 2, the control unit 12 has a hollow outer shaft 30 and an inner shaft 32 inserted in the outer shaft 30. The outer shaft 30 is rotatably fitted in a stationary base 36 through a first bearing 34. The inner shaft 32 is rotatably fitted in the outer shaft 30 through a second bearing 38. Thus, the outer and inner shafts 30 and 32 are rotatable relative to each other.

A first support arm 40 for supporting the first reaction container holder 4 is provided on one end of the inner shaft 32, and a first control mechanism 42 for controlling rotation of the inner shaft 32 is provided on the other end of the inner shaft 32.

A second support arm 44 for supporting the second container holder 6 is provided on one end of the outer shaft 30, and a second control mechanism 46 for controlling rotation of the outer shaft 30 is provided on the other end of the outer shaft 30.

The first control mechanism 42 has a first motor 50 having a first pinion 48, a first gear wheel 52 provided on the other end of the inner shaft 32 and engaged with the first pinion 48, a first detection plate 54 provided next to the first gear wheel 52, and a first detection sensor 56, provided on an outer circumferential edge portion of the first detection plate 54, for detecting the rotational state of the first detection plate 54, thus controlling rotation of the inner shaft 32.

The second control mechanism 46 has a second motor 60 having a second pinion 58, a second gear wheel 62 provided on the other end of the outer shaft 30 and engaged with the second pinion 58, a second detection plate 64 provided next to the second gear wheel 62, and a second detection sensor 66, provided on an outer circumferential edge portion of the second detection plate 64, for detecting the rotational state of the second detection plate 64, thus controlling rotation of the outer shaft 30.

The first and second motors 50 and 60 are connected to a control circuit 70 for controlling their drive and stop timings.

Grooves (not shown) corresponding in number to the reaction containers $4a, 4b, 4c, \ldots$, and $6a, 6b, 6c, \ldots$ provided to the first and second reaction container holders 4 and 6 are formed in the outer peripheral portions of the first and second detection plates 54 and 64, respectively. As a result, by detecting the presence/absence of these grooves through the first and second detection sensors 56 and 66, the plurality of reaction containers $4a, 4b, 4c, \ldots$, and $6a, 6b, 6c, \ldots$ can be individually aligned at the first reagent injecting portion 16, and the relative rotational speeds and rotational amounts of the outer and inner shafts 30 and 32 can be arbitrarily controlled.

The operation of the automatic analyzing apparatus having the arrangement described above will be described with reference to FIGS. 2 to 11. The analyzing cycle to be described below exemplifies AST testing. Note that the drawings referred to for a description only show a state in which the first and second reaction container holders 4 and 6 are sequentially rotated along the reaction line 2.

Figure 3:
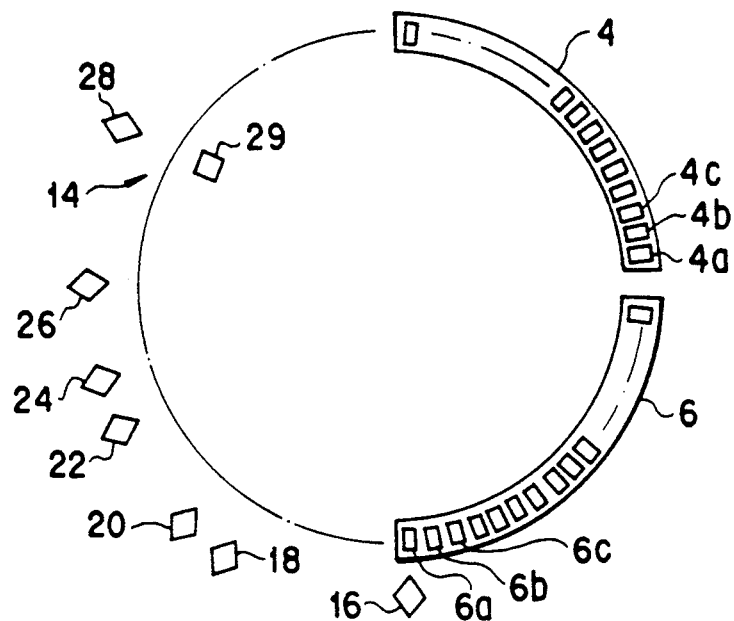
FIG. 3 is a view showing an initial stop state of the automatic analyzing apparatus.

FIG. 3 shows an initial stop state of the automatic analyzing apparatus of this embodiment.

In this state, the first reaction container 6a of the second reaction container holder 6 is placed at the first reagent injecting portion 16 where a first reagent containing aspartic acid is to be injected.

When the first reagent is injected in the first reaction container 6a, the first and second control mechanisms 42 and 46 are driven through the control circuit 70. More specifically, as shown in FIG. 2, the driving force of the second motor 60 is transmitted to the outer shaft 30 through the second pinion 58 and the second gear wheel 62 to rotate the outer shaft 30 at a predetermined speed. The first motor 50 is driven in synchronism with rotation of the outer shaft 30. Then, the driving force of the first motor 50 is transmitted to the inner shaft 32 through the first pinion 48 and the first gear wheel 52 to rotate the inner shaft 32 at the same rotational speed as that of the outer shaft 30.

Figure 4:
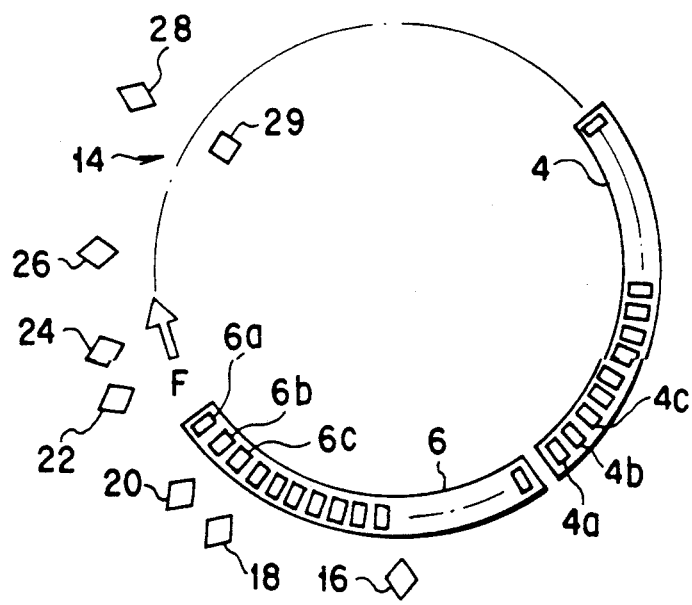
FIG. 4 is a view showing a state in which a first reaction container holder moves along a reaction line to follow a second reaction container holder.

As a result, as shown in FIG. 4, the second reaction container holder 6 is rotated at a predetermined speed in a direction indicated by an arrow F, and the first reaction container holder 4 is also rotated at the same speed in the same direction to follow the second reaction container holder 6.

The stop positions of the inner and outer shafts 32 and 30 are controlled with a high precision by detecting the presence/absence of the grooves of the first and second detection plates 54 and 64 by the first and second detection sensors 56 and 66, respectively.

Figure 5:
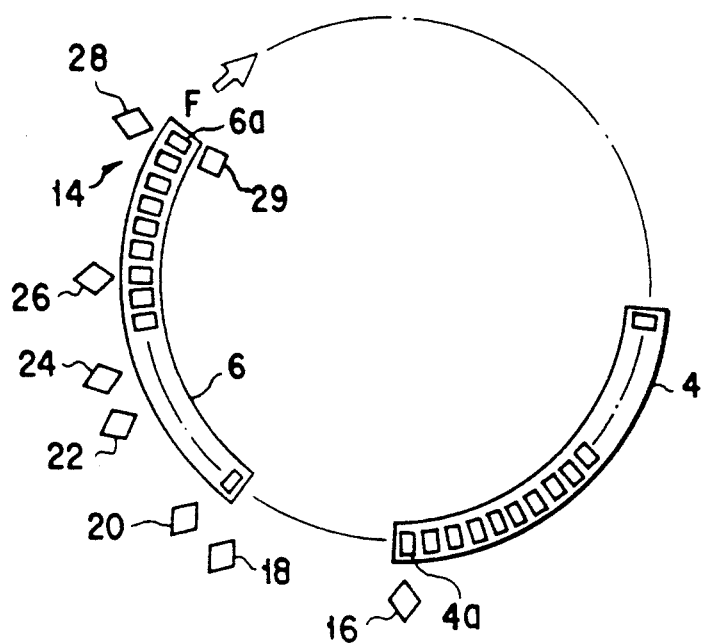
FIG. 5 is a view showing a state in which only the first reaction container holder is stopped and its first reaction container is placed at a first reagent injecting portion.

When the first reaction container 4a of the first reaction container holder 4 is brought to face the first reagent injecting portion 16, as shown in FIG. 5, the first motor 50 (refer to FIG. 2) is stopped by a detection signal output from the first detection sensor 56 (refer to FIG. 2). As a result, rotation of the first reaction container holder 4 is stopped, and the reaction container 4a is placed at the first reagent injecting portion 16.

While the first reagent is injected into the first reaction container 4a, the second motor 60 (refer to FIG. 2) is kept driven to rotate the second reaction container holder 6 in a direction indicated by an arrow F.

As a result, the second reaction container holder 6 which has passed through the photometric unit 14 is rotated along the reaction line 2 to approach the first reaction container holder 4.

Figure 6:
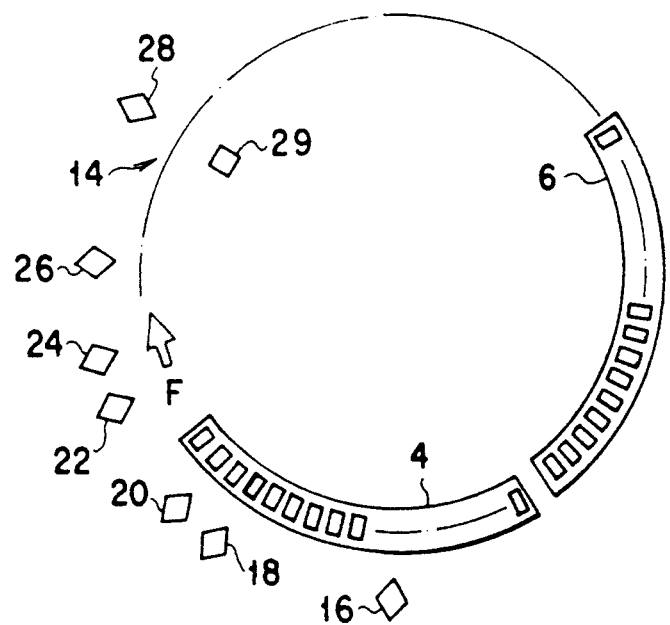
FIG. 6 is a view showing a state in which the second reaction container holder moves along the reaction line to follow the first reaction container holder.

When the second reaction container holder 6 approaches the first reaction container holder 4, as shown in FIG. 6, the first motor 50 (refer to FIG. 2) is driven to rotate the inner shaft 32. As a result, the first reaction container holder 4 is rotated in a direction indicated by an arrow F at the same speed as that of the second reaction container holder 6.

Figure 7:
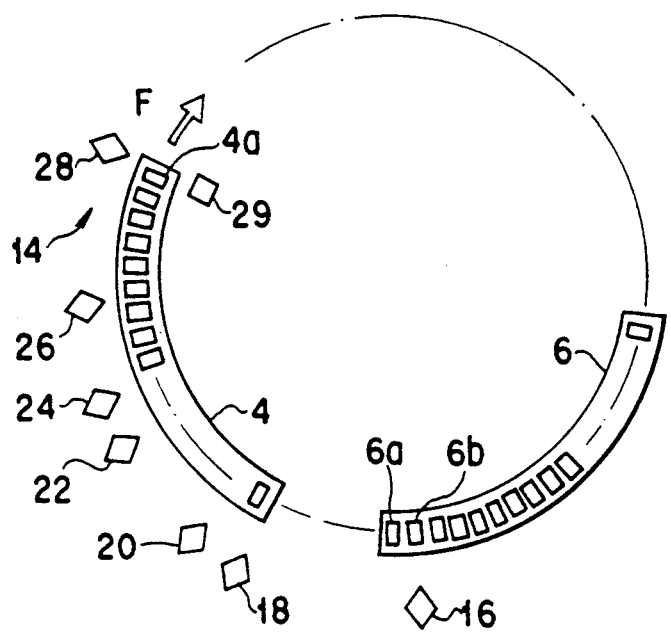
FIG. 7 is a view showing a state in which only the second reaction container holder is stopped and its second reaction container is placed at the first reagent injecting portion.

The second reaction container holder 6 which has rotated to follow the first reaction container holder 4 is stopped when its second reaction container 6b next to the reaction container 6a is brought to face the first reagent injecting portion 16, as shown in FIG. 7. This stopping operation will be described in detail.

For example, the grooves are counted, on the basis of a groove (assume this groove as the first groove) which is counted when the first reaction container 6a is placed at the first reagent injecting portion 16, through the second detection sensor 66 until the second detection plate 64 is rotated by one turn. When a groove (i.e., the second groove) next to the first groove is detected, the control circuit 70 is operated based on a signal output from the second detection sensor 66 to stop the second motor 60. As a result, the second reaction container 6b is placed at the first reagent injecting portion 16.

While the first reagent is injected in the reaction container 6b, the first reaction container holder 4 is rotated in a direction indicated by an arrow F in FIG. 7 and approaches the second reaction container holder 6 after the reaction container 4a passes through the photometric unit 14. As the first reaction container holder 4 approaches the second holder 6, the control circuit 70 is operated again to move the second reaction container holder 6 in a direction indicated by an arrow F in FIG. 8.

Figure 8:
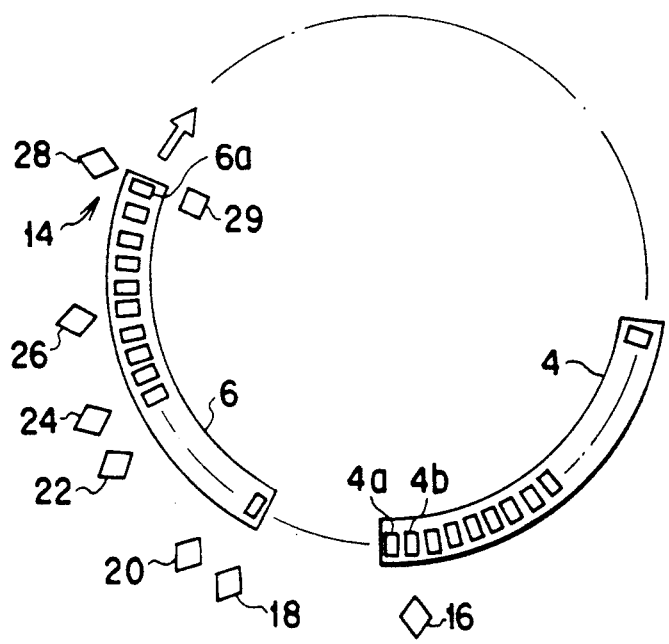
FIG. 8 is a view showing a state in which only the first reaction container holder is stopped and its second reaction container is placed at the first reagent injecting portion.

As a result, the second reaction container 4b of the first reaction container holder 4 is placed at the first reagent injecting portion 16, as shown in FIG. 8.

The above operation is repeated to place the eighth reaction container 6h of the second reaction container holder 6 at the first reagent injecting portion 16, as shown in FIG. 9. More specifically, when the first and second container holders 4 and 6 are sequentially rotated by seven turns, when counted from the initial state, along the reaction line 2 in the direction indicated by the arrow F, the reaction container 6h is placed at the first reagent injecting portion 16.

When the reaction container 6h of the second reaction container holder 6 is placed at the first reagent injecting portion 16, as shown in FIG. 9, the first reaction container 6a is positioned at the liquid sample injecting portion 18 where the liquid sample, e.g., blood, as an AST testing target is to be injected.

As a result, the liquid sample is injected in the first reaction container 6a in which the first reagent has already been contained, and the reagent is injected in the eighth reaction container 6h simultaneously. During this period of time, the first reaction container holder 4 is rotated along the reaction line 2. As the first reaction container holder 4 approaches the second holder 6, the second reaction container holder 6 is rotated once again.

When the above operation is repeated, the tenth reaction container 6j of the second reaction container holder 6 is placed at the first reagent injecting portion 16, as shown in FIG. 10.

As shown in FIG. 10, when the reaction container 6j of the second reaction container holder 6 is placed at the first reagent injecting portion 16, the first reaction container 6a is placed at the first agitating portion 20 for agitating the first reagent and the liquid sample injected in it. The third reaction container 6c is positioned at the liquid sample injecting portion 18 for injecting the liquid sample such as blood as an AST testing target.

As a result, while the first reaction container holder 4 is rotated, the first reagent and the liquid sample contained in the reaction container 6a are agitated, and simultaneously the first reagent and the liquid sample are injected into the reaction containers 6j and 6c, respectively.

As the first reaction container holder 4 approaches the second reaction container holder 6, the second reaction container holder 6 moves along the reaction line 2 again. When the second reaction container holder 6 passes through the photometric unit 14, the reaction process between the liquid sample and the first reagent in the reaction container 6a is optically measured, thereby performing optical analysis of the concentration of a chemical component of the liquid sample.

When this operation is repeated, the first reaction container 6a of the second reaction container holder 6 is sequentially placed at the second reagent injecting portion 22 for injecting a second reagent containing α-ketoglutaric acid and the second agitating portion AST testing is completed by these cycles.

When optical analysis of the reaction container 6a is completed, the interior of the reaction container 6a is cleaned at the reaction container cleaning portion 26.

The above operation is repeated for the remaining reaction containers 6b, 6c, . . . to perform predetermined analysis.

The reaction containers 4a, 4b, 4c, . . . of the first reaction container holder 4 are subjected to the same processing cycle as those for the second reaction container holder 6.

In the conventional analyzing apparatus, a plurality of reaction containers are continuously arranged along a reaction line and are moved or stopped simultaneously to perform the analysis. For this reason, when the analysis processing capability is given as 6 seconds/cycle, moving and stopping operations for the reaction containers must be divided into, e.g., 3 seconds for movement and 3 seconds for stop.

In contrast to this, in the automatic analyzing apparatus of the embodiment described above, the sufficient empty portion 10 is reserved in the reaction line 2, and the plurality of reaction containers 4a, 4b, 4c, . . . and 6a, 6b, 6c, . . . are respectively provided in the two reaction container holders 4 and 6. Therefore, even when the analysis processing capability for performing optical analysis of the liquid sample through the photometric unit 14 is set to 6 seconds/cycle, while one reaction container holder 6 is being moved, the other reaction container holder 6 can be stopped.

Figure 11:
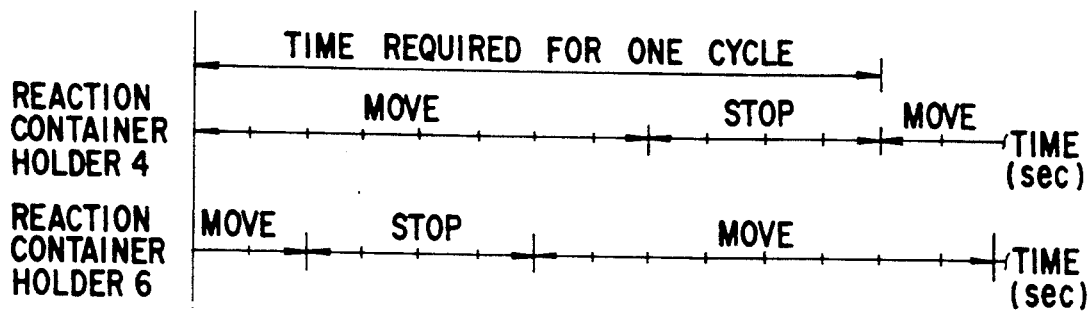
FIG. 11 shows timing charts indicating a time required for one cycle of each of the first and second reaction container holders.

As a result, in the automatic analyzing apparatus of the above embodiment, as shown in FIG. 11, while the analysis processing capability is kept at 6 seconds/cycle, a time required for one cycle of each of the first and second reaction container holders 4 and 6 be set to 12 seconds, a time required for one rotation of each of the first and second reaction container holder 4 and 6 can be set to 8 seconds, and a stop time can be prolonged to 4 seconds.

That is, according to the apparatus of the above embodiment, since the moving time of the reaction containers can be kept longer than that in the conventional apparatus within the same analysis processing capable time as that of the conventional apparatus, a photometric operation can be stably performed with a high precision. Also, since the stop time of the reaction containers can be kept longer than that in the conventional apparatus, cleaning and so on of the reaction containers can be sufficiently performed. As a result, testing of the liquid sample such as blood can be performed with a higher precision than in the conventional apparatus.

The present invention is not limited to the arrangement of the embodiment described above. For example, the time required for one cycle may be set to 9 seconds, a time required for one rotation of the first and second reaction container holders 4 and 6 may be set to 6 seconds, the stop time may be set to 3 seconds, and the analysis processing capability may be set to 4.5 seconds/cycle.

In this case as well, the performance of the apparatus including optical analysis and injection and agitation of the liquid sample and reagents can be maintained at a high precision.

Figure 12:
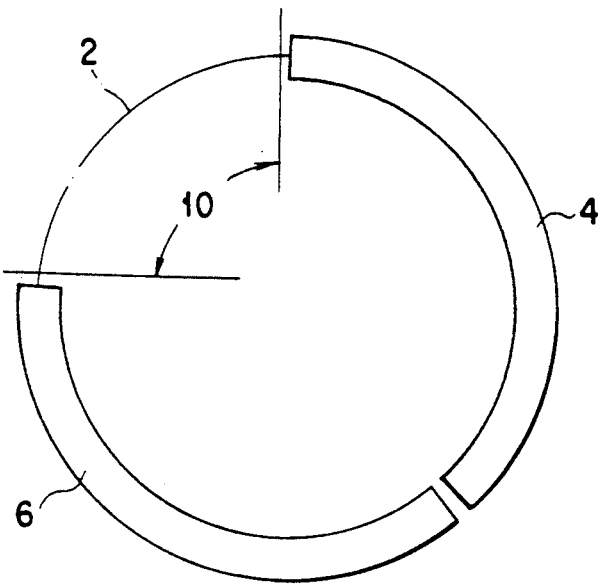
FIG. 12 is a view showing another arrangement of the first and second reaction container holders.

The lengths of the first and second reaction container holders 4 and 6 may be increased, as shown in FIG. 12. That is, the distance of the empty portion 10 between the reaction container holders 4 and 6 may be decreased within a range capable of obtaining a necessary stop time.

In this case, the time required for one rotational movement of each of the reaction container holders 4 and 6 becomes 8 seconds, the stop time becomes 2 seconds, and the analysis processing capability is set to 5 seconds/cycle.

In this case as well, the performance of the apparatus including optical analysis and injection and agitation of the liquid sample and reagents can be maintained with a high precision.

If the reaction time is set long or the number of processing steps is large, the reaction line 2 becomes long. If the number of processing steps is small, the reaction container holders 4 and 6 become short. The longer the reaction line 2 or the shorter the reaction container holders 4 and 6, the more delayed the timing at which the two reaction container holders 4 and 6 follow each other. In this case, the number of reaction container holders may be increased to adjust the timing. A newly added holder may be used merely as a dummy holder to maintain a predetermined timing.

When such a dummy holder is used, it may be rotated together with a reaction container holder while the timing is controlled so that it may not be subjected to distribution processing.

In particular, when dummy holders corresponding in number to the reaction container holders are to be used, they are integrally coupled to the ends of the corresponding reaction container holders and rotated so that continuous distribution processing may be sequentially performed starting from the reaction container at the beginning in the same manner as in the embodiment described above. When the dummy holders are used, the rotational speeds of the reaction container holders can be decreased to maintain a high photometric precision.

In this manner, the number of reaction container holders which are caused to rotate and follow may be three or more if the entire apparatus is arranged such that the plurality of reaction containers provided to the respective reaction container holders are sequentially and continuously subjected to distribution processing.

To adjust the processing timing e.g., distribution processing to a predetermined optimum cycle, the length of a dummy holder need not be necessarily equal to that of the corresponding reaction container holder.

In order to easily maintain high-precision rotation/stop control of the apparatus, the lengths of the respective reaction container holders to be subjected to analysis may preferably be equal to each other, and the number of reaction containers provided to the respective reaction container holders may preferably be the same.

In the embodiment described above, two reaction container holders are rotationally moved along the circular reaction line to follow each other. However, two or more reaction container holders may be reciprocated along an arcuated reaction line having two end portions respectively provided with photometric units.

The plurality of reaction containers provided in the respective reaction container holders may be concentrically arranged in a plurality of arrays to the reaction container holders. In this case, however, as the plurality of arrays of reaction containers are arranged, it is difficult to perform light measurement from the side surface of each of the reaction container holders. Therefore, a photometric unit is provided vertically above the plurality of reaction containers to perform light measurement in the vertical direction.

The position of the photometric unit 14 is not limited to the one described above. The photometric unit 14 can be placed at an arbitrary position as far as it does not fall to a stop position of the first or second reaction container holder 4 or 6.

The positions of the first and second detection sensors 56 and 66 can be arbitrarily set as far as they can detect grooves o the outer circumferential portions of first and second corresponding detection plates 54 and 56, respectively.

The reaction line 2 can house all the components described above and is effectively utilized, e.g., to add other components.

The arrangement of the first reagent injecting portion 16 and the second liquid sample injecting portion 18 can be reversed. A photometric operation of a reaction container containing only the reagent or liquid sample can be omitted. If not, the nature or presence of the reagent or liquid sample may be confirmed.

Furthermore, when the first reagent and the liquid sample are distributed simultaneously, the number of injecting portions 16 and 18 may be reduced to one.

The second reagent injecting portion 22 is not always necessary depending on the measurement principle and can be omitted if the processing cycle is set to an optimum one as required.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An automatic analyzing apparatus comprising:
   a plurality of reaction container holders which are independently movable along a circulation line having a single center of rotation, said reaction container holders being rotated around the single center of rotation, each of said reaction container holders holding a plurality of reaction containers and having a length which is no greater than ½ of a circumference of the circulation line;
   injector means, arranged along the circulation line, for injecting at least one of a sample and a reagent into the reaction containers;
   a photometric unit, arranged along the circulation line, for optically analyzing a concentration of chemical components of the sample injected into the reaction containers;
   rotating means for rotating the reaction container holders independently of one another; and
   a control unit for controlling the rotating means to cause the reaction container holders to be continuously rotated and to temporarily stop rotation of a respective reaction container holder when said respective reaction container holder comes to a position corresponding to the injector means, while at least one other reaction container holder is continuously rotated.

2. An apparatus according to claim 1, wherein each of said reaction container holders has an arc shape having a radius of curvature substantially the same as a radius of curvature of the circulation line.

3. An apparatus according to claim 1, wherein said circulation line is endless and has a circular shape.

4. An apparatus according to claim 3, wherein said control unit includes means for controlling the rotating means for causing the reaction container holders to be rotated in the same direction independently of one another.

5. An apparatus according to claim 3, wherein each of said reaction container holders has a length which is approximately ¼ of the circumference of the circulation line.

6. An apparatus according to claim 3, wherein each of said reaction container holders has a length which is approximately ⅛ of the circumference of the circulation line.

7. An apparatus according to claim 3, wherein each of said reaction container holders has an arc shape having a radius of curvature substantially the same as a radius of curvature of the circulation line.

8. An apparatus according to claim 7, wherein each of said reaction container holders has a length which is approximately ¼ of the circumference of the circulation line.

9. An apparatus according to claim 7, wherein each of said reaction container holders has a length which is approximately ⅛ of the circumference of the circulation line.

10. An automatic analyzing method comprising the steps of:
    causing a rotating means to rotate a plurality of reaction container holders along a circulation line having a single center of rotation such that the reaction container holders are rotated independently of one another around the single center of rotation, each of said reaction container holders holding a plurality of reaction containers and having a length which is no greater than ½ of a circumference of the circulation line;
    temporarily stopping rotation of a respective reaction container holder when said respective reaction container holder comes to a position corresponding to an injector, while at least one other reaction container holder is continuously rotated said injector means being arranged along the circulation line,
    injecting at least one of a sample and a reagent into the reaction containers of the reaction container holder which is temporarily stopped at said position; and
    causing a photometric unit to optically analyze a concentration of chemical components of the sample injected into the reaction containers of remaining reaction container holders which are being rotated when the injection step is executed.

11. A method according to claim 10, wherein each of said reaction container holders has an arc shape having a radius of curvature substantially the same as a radius of curvature of the circulation line.

12. A method according to claim 10, wherein said circulation line is endless and has a circular shape.

13. A method according to claim 12, wherein:
said rotating means is controlled by the control unit; and
said control unit controls the rotating means such that the reaction container holders are rotated in the same direction independently of one another.

14. A method according to claim 12, wherein each of said reaction container holders has a length which is approximately ¼ of the circumference of the circulation line.

15. A method according to claim 12, wherein each of said reaction container holders has a length which is approximately ⅓ of the circumference of the circulation line.

16. A method according to claim 12, wherein each of said reaction container holders has an arc shape having a radius of curvature substantially the same as a radius of curvature of the circulation line.

17. A method according to claim 16, wherein each of said reaction container holders has a length which is approximately ¼ of the circumference of the circulation line.

18. A method according to claim 16, wherein each of said reaction container holders has a length which is approximately ⅓ of the circumference of the circulation line.

* * * * *